US012746267B2

(12) United States Patent
Ovadia

(10) Patent No.: US 12,746,267 B2
(45) Date of Patent: Sep. 29, 2026

(54) COMPOSITIONS AND METHODS OF USING SAME FOR TREATING AMYOTROPHIC LATERAL SCLEROSIS (ALS)

(71) Applicant: Immunity Pharma Ltd., Mevasseret Zion (IL)

(72) Inventor: Eran Ovadia, Mevasseret Zion (IL)

(73) Assignee: Immunity Pharma Ltd., Mevasseret Zion (IL)

(*) Notice: Subject to any disclaimer, the term of this patent is extended or adjusted under 35 U.S.C. 154(b) by 139 days.

(21) Appl. No.: 17/105,557

(22) Filed: Nov. 26, 2020

(65) Prior Publication Data

US 2021/0100869 A1 Apr. 8, 2021

Related U.S. Application Data

(63) Continuation-in-part of application No. PCT/IL2019/050619, filed on May 30, 2019.

(60) Provisional application No. 62/678,316, filed on May 31, 2018.

(51) Int. Cl.

| | |
|---|---|
| ***A61K 38/08*** | (2019.01) |
| ***A61K 9/00*** | (2006.01) |
| ***A61P 25/28*** | (2006.01) |

(52) U.S. Cl.

CPC ............ *A61K 38/08* (2013.01); *A61K 9/0019* (2013.01); *A61P 25/28* (2018.01)

(58) Field of Classification Search

CPC ...... A61K 38/08; A61K 9/0019; A61K 47/02; A61P 25/28; A61P 25/00

See application file for complete search history.

(56) References Cited

U.S. PATENT DOCUMENTS

2002/0037908 A1 3/2002 Douglas et al.
2003/0140362 A1* 7/2003 Macejak ............ C12N 15/1131 435/5
2008/0267983 A1 10/2008 Herkel et al.
2014/0228420 A1 8/2014 Yoncoka
2016/0033529 A1* 2/2016 Ovadia ................ A61K 38/185 435/7.92

FOREIGN PATENT DOCUMENTS

JP 2008-510796 4/2008
JP 2010-509345 5/2010
JP 7350019 9/2023
RU 2 547 441 4/2015
WO WO 2006/021954 3/2006
WO WO-2006046109 A1 * 5/2006 ............. A61K 31/40
WO WO-2008150305 A1 * 12/2008 ........... A61K 31/337
WO WO 2012/160563 11/2012
WO WO 2016/040877 3/2016
WO WO 2016/077687 5/2016
WO WO-2016077687 A1 * 5/2016 ............. A61P 21/02
WO WO 2019/229757 12/2019

OTHER PUBLICATIONS

Izutsu, Chapter 22 of Therapeutic Proteins Methods and Protcols, Ed. By Smales and James, Humana Press 2005, pp. 287-292 (Year: 2005).*
Bell, Biotechnol. Prog. 1997, 13, 342-346 (Year: 1997).*
Simon et al., Ann Neurol 2014;76:643-657 (Year: 2014).*
Blog page from ALS.NET, downloaded May 13, 2023 from https://www.als.net/news/50-years-with-als-what-can-we-learn-from-slow-progressors-like-stephen-hawking/, 2023 (Year: 2023).*
ThermoFisher Balanced Salt Solutions screen shot, taken from the internet Sep. 18, 23 (Year: 2023).*
Usach et al., Adv Ther (2019) 36:2986-2996 (Year: 2019).*
Grasela et al., Summary from Comprehensive Medicinal Chemistry III, 2017, summary from pp. 51-82, 2 pages (Year: 2017).*
Doyle, Clinical Procedures for Safer Patient Care, 2015, CampusOpenEd, chapter 7.5 (Year: 2015).*
Cell, 2023, 12 1523, 33 pages (Year: 2023).*
ALS Therapy Development Institute, downloaded from the world-wide web, 2025, 8 pages (Year: 2025).*
The Harvard Gazette, entitled High-calorie feeding may slow progression of ALS, author Sue McGreevey, Feb. 27, 2014, 4 pages (Year: 2014).*
Translation Dated Dec. 16, 2022 of Request for Examination Dated Nov. 17, 2022 From the (ROSPATENT), Federal Government Institution of Industrial Property of the Federal Service of Intellectual Property, Patents and Trademark of the Russian Federation Re. Application No. 2020143087. (9 pages).
Communication Pursuant to Rule 164(1) EPC [Supplementary Partial European Seach Report and the Provisional Opinion] Dated Mar. 28, 2022 From the European Patent Office Re. Application No. 19811026.4. (14 Pages).
ClinicalTrials "A Study of IPL344 in the Treatment of ALS Patients", ClinicalTrials.gov, XP055900028, Clinical Trials.gov Identifier: NCT03652805, p. 1-9, Aug. 29, 2018.
Herkel et al. "Activation of the Akt-CREB Signalling Axis by A Proline-Rich Heptapeptide Confers Resistance to Stress-Induced Cell Death and Inflammation", Immunology, XP071277131, 151(4): 474-480, May 16, 2017.
Supplementary European Seach Report and the European Search Opinion Dated Jun. 29, 2022 From the European Patent Office Re. Application No. 19811026.4. (11 Pages).
Office Action Dated Apr. 24, 2023 From the Israel Patent Office Re. Application No. 279108. (4 Pages).

(Continued)

*Primary Examiner* — Joseph Fischer

(57) ABSTRACT

Compositions and methods of using same for treating Amyotrophic Lateral Sclerosis (ALS) are provided. Accordingly there is provided a method of treating ALS in a human subject in need thereof, the method comprising intravenously (IV) administering to the subject 2-5 mg/kg of a peptide comprising an amino acid sequence as set forth in SEQ ID NO: 1. Also provided are compositions and unit dosage forms comprising a peptide comprising an amino acid sequence as set forth in SEQ ID NO: 1.

6 Claims, 2 Drawing Sheets

Specification includes a Sequence Listing.

(56) References Cited

OTHER PUBLICATIONS

Request for Examination Dated Nov. 17, 2022 From the (ROSPATENT), Federal Government Institution of Industrial Property of the Federal Service of Intellectual Property, Patents and Trademark of the Russian Federation Re. Application No. 2020143087 with English Summary. (12 pages).
Notice of Reason(s) for Rejection Dated Feb. 28, 2023 From the Japan Patent Office Re. Application No. 2020-565903 and Its Translation Into English. (10 Pages).
International Preliminary Report on Patentability Dated Dec. 10, 2020 From the International Bureau of WIPO Re. Application No. PCT/IL2019/050619. (7 Pages).
International Search Report and the Written Opinion Dated Oct. 28, 2019 From the International Searching Authority Re. Application No. PCT/IL2019/050619. (14 Pages).
Invitation to Pay Additional Fees Dated Sep. 5, 2019 From the International Searching Authority Re. Application No. PCT/IL2019/050619. (2 Pages).
Immunity Pharma "Immunity Pharma Announces Promising Interim Results of Its Phase 1/2a Study With IPL344 in ALS", Immunity Pharma, Ltd., p. 1-6, Sep. 10, 2020.
Ray "Investigational Treatment IPL344 Safely Slows ALS Progression in Small Phase 1/2a Trial", ALS News Today, p. 1-10, Sep. 17, 2020.
Examination Report Dated Mar. 19, 2025 From the Instituto Mexicano de la Propiedad Industrial, Secretaria de Economia, Direccion Divisional de Patentes Re. Application No. MX/a/2020/012532 and Its Translation Into English. (16 Pages).
Request for Examination and Search Report Dated Sep. 20, 2024 From the (ROSPATENT), The Federal Service for Intellectual Property, Patents and Trademarks of the Russian Federation Re. Application No. 2023125245 and Its Summary in English. (12 Pages).
Requisition by the Examiner Dated Jun. 17, 2024 From the Innovation, Science and Economic Development Canada, Canadian Intellectual Property Office Re. Application No. 3,099,846. (4 Pages).
Request for Examination and Search Report Dated May 8, 2024 From the (ROSPATENT), The Federal Service for Intellectual Property, Patents and Trademarks of the Russian Federation Re. Application No. 2023125245. (4 Pages).
Examination Report Dated Feb. 14, 2025 From the Australian Government, IP Australia Re. Application No. 2019277920. (3 Pages).
Request for Examination and Search Report Dated Feb. 18, 2025 From the (ROSPATENT), Federal Government Institution of Industrial Property of the Federal Service of Intellectual Property, Patents and Trademark of the Russian Federation Re. Application No. 2023125245 and Its Translation Into English. (14 Pages).
Examination Report Dated Feb. 14, 2024 From the Australian Government, IP Australia Re. Application No. 2019277920. (4 Pages).
Translation Dated May 17, 2024 of Notice of Violation Unity Requirements Dated May 8, 2024 From the (ROSPATENT), The Federal Service for Intellectual Property, Patents and Trademarks of the Russian Federation Re. Application No. 2023125245. (3 Pages).
Examination Report Dated Aug. 8, 2024 From the Australian Government, IP Australia Re. Application No. 2019277920. (3 Pages).
Examination Report Dated Oct. 15, 2024 From the Instituto Mexicano de la Propiedad Industrial, Direccion Divisional de Patentes Re. Application No. MXa/2020/012532. and Its Translation Into English. (12 Pages).
Examination Report Dated Jan. 30, 2026 From the Australian Government, IP Australia Re. Application No. 2025201060. (3 Pages).
Communication Pursuant to Article 94(3) EPC Dated Nov. 24, 2025 From the European Patent Office Re. Application No. 19811026.4 (6 Pages).

* cited by examiner

COMPOSITIONS AND METHODS OF USING SAME FOR TREATING AMYOTROPHIC LATERAL SCLEROSIS (ALS)

RELATED APPLICATIONS

This application is a US Continuation-In-Part (CP) of PCT Patent Application No. PCT/IL2019/050619 filed on May 30, 2019, which claims the benefit of priority under 35 USC § 119(e) of U.S. Provisional Patent Application No. 62/678,316 filed on May 31, 2018. The contents of the above applications are all incorporated by reference as if fully set forth herein in their entirety.

SEQUENCE LISTING STATEMENT

The ASCII file, entitled 83591SequenceListing.txt, created on Nov. 26, 2020, comprising 485 bytes, submitted concurrently with the filing of this application is incorporated herein by reference.

FIELD AND BACKGROUND OF THE INVENTION

The present invention, in some embodiments thereof, relates to compositions and methods of using same for treating Amyotrophic Lateral Sclerosis (ALS).

Amyotrophic Lateral Sclerosis (ALS) is a multisystem neurodegenerative disorder, in which patients develop progressive paralysis involving all skeletal muscles as well as the bulbar and respiratory muscles involved in breathing, speaking and swallowing. The disease typically strikes adults over the age of 50, with the prevalence highest among those in their 70s. The etiology of the disease has not yet been fully elucidated. It is generally accepted that misfolded proteins, primarily TDP43 in the sporadic, non-genetic disease, and other proteins such as superoxide dismutase type-1 (SOD1) in the genetic disease, accumulate within the central nervous system (CNS) and lead to unfolded protein response, also known as Endoplasmic Reticulum (ER) stress. ER stress initially induces increased production of chaperones handling protein folding and reduced protein production, but as the stress continues, it leads to apoptosis (Walker 2011, Lautenschlaeger 2012, Verma 2013, Mori 2013).

Currently, two drugs have been approved by the FDA for the treatment of ALS, Rilutek® (riluzole) and Radicava® (edaravone), which have an estimated moderate effect of a three months extension in patient survival. Other treatments such as Nuedexta are available for symptom management and to improve the quality of life of patients; Nuedexta has been approved for the treatment of pseudobulbar affect (emotional lability) in patients with ALS. However, to date, no cure for ALS is available.

Dysfunction in the Akt signaling process is common to major age-related neuro-degenerative diseases (Wu 2010). Recently reported studies have shown close correlations between the levels of Akt and trophic factors, the natural activators of the Akt pathway, and progression rate of the disease in ALS patients (Koh 2012, Yin 2012): ALS patients with high total Akt level in muscle tissues have better overall survival. Thus, restoring effective Akt signaling can elicit cell survival processes and inhibit tissue degeneration.

The peptide LPPLPYP (SEQ ID NO: 1, also known as Stressin-1 and IPL344) is a short 7 amino acids peptide that protects cells of various types from pro-apoptotic pressures and activates the Akt signaling system. The structure of IPL344 resembles the binding sites of adaptor proteins; and its mechanism of action seems to be by mimicking such proteins and activating cell protective processes via Akt and possibly other pathways.

International Patent Application Publication Nos.: WO 2006/021954 and WO2012/160563 disclose the use of LPPLPYP (SEQ ID NO: 1) peptide for treating inflammatory and autoimmune diseases such as ALS.

SUMMARY OF THE INVENTION

According to an aspect of some embodiments of the present invention there is provided a method of treating amyotrophic lateral sclerosis (ALS) in a human subject in need thereof, the method comprising intravenously (IV) administering to the subject 2-5 mg/kg of a peptide comprising an amino acid sequence as set forth in SEQ ID NO: 1, thereby treating the ALS in the subject.

According to an aspect of some embodiments of the present invention there is provided a method of treating amyotrophic lateral sclerosis (ALS) in a human subject in need thereof, the method comprising repetitively intravenously (IV) administering to the subject 1.7-5 mg/kg of a peptide comprising an amino acid sequence as set forth in SEQ ID NO: 1 in a dose escalating manner, thereby treating the ALS in the subject.

According to some embodiments of the invention, the method comprising monitoring the subject by ALS Functional Rating Scale (ALSFRS); respiratory function; muscle strength and/or cognitive function.

According to an aspect of some embodiments of the present invention there is provided a peptide comprising an amino acid sequence as set forth in SEQ ID NO: 1 for use in treating amyotrophic lateral sclerosis (ALS) in a human subject in need thereof, wherein the peptide is administered to the subject intravenously (IV) at a dose comprising 2-5 mg/kg of the peptide.

According to an aspect of some embodiments of the present invention there is provided a peptide comprising an amino acid sequence as set forth in SEQ ID NO: 1 for use in treating amyotrophic lateral sclerosis (ALS) in a human subject in need thereof, wherein the peptide is administered to the subject repetitively intravenously (IV) in a dose escalating manner comprising 1.7-5 mg/kg of the peptide.

According to some embodiments of the invention, the dose escalating is by 0.3-0.5 mg/kg.

According to some embodiments of the invention, the dose escalating is effected every 2-7 days.

According to some embodiments of the invention, the dose escalating is stopped in the event of hypersensitivity or an adverse event (AE) related to the peptide.

According to some embodiments of the invention, the ALS is ALS-associated depression.

According to some embodiments of the invention, the ALS is rapid progression ALS.

According to some embodiments of the invention, the ALS is non-slow progression ALS.

According to an aspect of some embodiments of the present invention there is provided a composition comprising 5% peptide comprising an amino acid sequence as set forth in SEQ ID NO: 1, wherein the composition has a pH of 4.5-5.5.

According to some embodiments of the invention, the composition comprising PBS and/or dPBS.

According to some embodiments of the invention, the composition comprising saline.

According to some embodiments of the invention, the peptide is formulated in a composition comprising 5% peptide comprising an amino acid sequence as set forth in SEQ ID NO: 1, Wherein the composition has a pH of 4.5-5.5.

According to some embodiments of the invention, the composition is packaged in a glass vial.

According to some embodiments of the invention, the composition is extractable.

According to some embodiments of the invention, the administering is effected on a daily basis.

According to some embodiments of the invention, the administering is by bolus injection.

According to some embodiments of the invention, the administering is by IV infusion.

According to some embodiments of the invention, the peptide is administered to the subject on a daily basis.

According to some embodiments of the invention, the peptide is administered to the subject by bolus injection.

According to some embodiments of the invention, the peptide is administered to the subject by IV infusion.

According to some embodiments of the invention, the 1.7-5 mg kg is 2-5 mg/kg.

According to some embodiments of the invention, the 2-5 mg/kg is 2.5-4.5 mg/kg.

According to some embodiments of the invention, the 2-5 mg/kg is 3-4 mg/kg.

According to some embodiments of the invention, the 2-5 mg/kg is about 3.2 mg/kg.

According to some embodiments of the invention, the 2-5 mg/kg is about 4.5 mg/kg.

According to some embodiments of the invention, the subject has rapid progression ALS and/or ALS-associated depression.

According to an aspect of some embodiments of the present invention there is provided a unit dosage form comprising 140-350 mg peptide comprising an amino acid sequence as set forth in SEQ ID NO: 1 formulated for intravenous (IV) administration.

According to some embodiments of the invention, the 140-350 mg is 140-315 mg.

According to some embodiments of the invention, the 140-350 mg is 210-280 mg.

According to some embodiments of the invention, the 140-350 mg is about 225 mg.

According to some embodiments of the invention, the 140-350 mg is about 315 mg.

According to an aspect of some embodiments of the present invention there is provided a unit dosage form comprising 35-90 mg peptide comprising an amino acid sequence as set forth in SEQ ID NO: 1 formulated for intravenous (IV) administration.

According to some embodiments of the invention, the 35-90 mg is 35-80 mg.

According to some embodiments of the invention, the 35-90 mg is 50-70 mg.

According to some embodiments of the invention, the 35-90 mg is about 60 mg.

According to some embodiments of the invention, the 35-90 mg is about 80 mg.

According to some embodiments of the invention, the peptide is formulated in a composition comprising 5% peptide comprising an amino acid sequence as set forth in SEQ ID NO: 1, wherein the composition has a pH of 4.5-5.5.

According to some embodiments of the invention, the unit dosage form being packaged in a glass vial.

According to some embodiments of the invention, the unit dosage form being extractable.

According to some embodiments of the invention, the peptide is formulated in a composition comprising PBS and/or dPBS.

According to some embodiments of the invention, the PBS and/or the dPBS comprise calcium and magnesium.

According to some embodiments of the invention, the peptide is formulated in a composition comprising saline.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWING(S)

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

DESCRIPTION OF SPECIFIC EMBODIMENTS OF THE INVENTION

Figure 1:
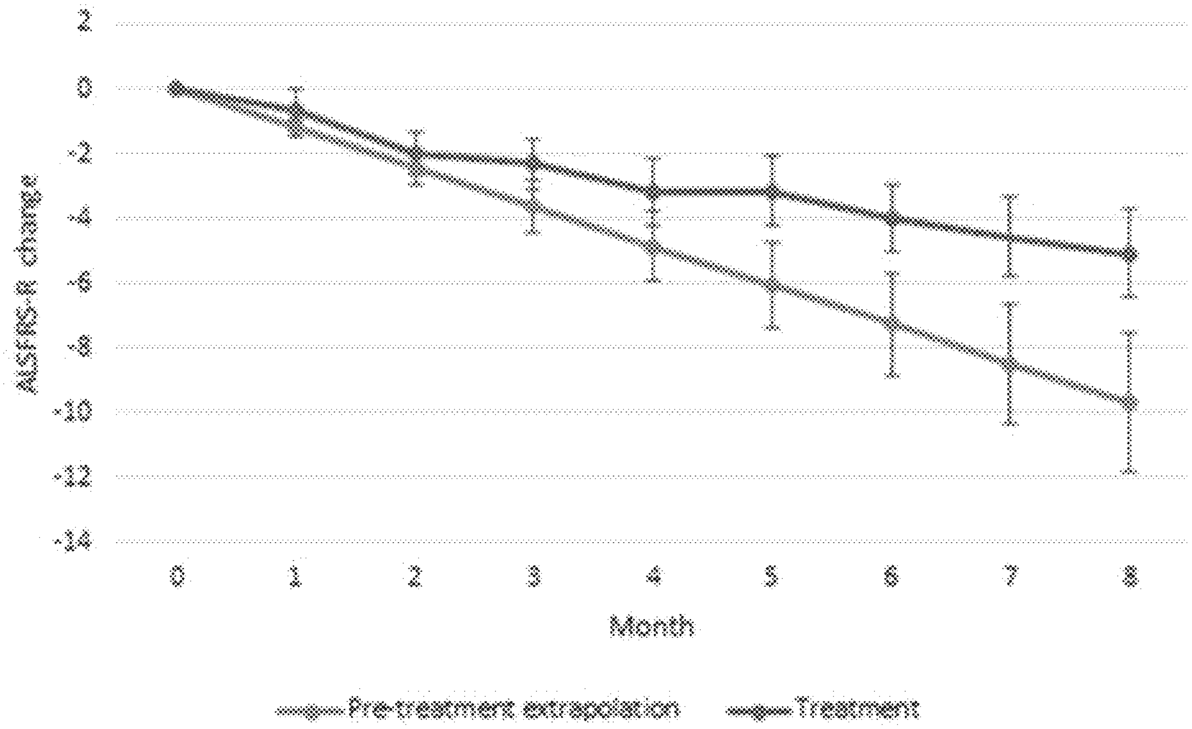
FIG. 1 is a graph demonstrating ALSFRS-R change from baseline in ALS patients treated with 3.2 mg/kg IPL344 as compared to the change from baseline calculated assuming the progression rates of those patients prior to treatment continues in a linear manner.

The present invention, in some embodiments thereof, relates to compositions and methods of using same for treating Amyotrophic Lateral Sclerosis (ALS).

Amyotrophic Lateral Sclerosis (ALS) is a multisystem neurodegenerative disorder, in which patients develop progressive paralysis involving all skeletal muscles as well as the bulbar and respiratory muscles involved in breathing, speaking and swallowing.

The peptide LPPLPYP (SEQ ID NO: 1, also known as IPL344 and Stressin-1) is a short 7 amino acids peptide that protects cells of various types from proapoptotic pressures and activates the Akt signaling system; and has been suggested for treating inflammatory and autoimmune diseases such as ALS.

The present inventors have now developed, through laborious experimentation and screening an effective novel therapeutic dose and regimen and formulation employing LPPLPYP (SEQ ID NO: 1) for the treatment of ALS in human patients.

Thus, according to a first aspect of the present invention, there is provided a method of treating amyotrophic lateral sclerosis (ALS) in a human subject in need thereof, the method comprising intravenously (IV) administering to the subject 2-5 mg kg of a peptide comprising an amino acid sequence as set forth in SEQ ID NO: 1, thereby treating the ALS in the subject.

According to another aspect of the present invention, there is provided a peptide comprising an amino acid sequence as set forth in SEQ ID NO: 1 for use in treating amyotrophic lateral sclerosis (ALS) in a human subject in need thereof, wherein said peptide is administered to said subject intravenously (IV) at a dose comprising 2-5 mg/kg of said peptide.

According to another aspect of the present invention, there is provided a use of a peptide comprising an amino acid sequence as set forth in SEQ ID NO: 1 in the manufacture of a medicament for intravenous (IV) administration for treating amyotrophic lateral sclerosis (ALS) in a human subject in need thereof, wherein said medicament is administered to said subject at a dose comprising 2-5 mg/kg of said peptide.

According to another aspect of the present invention, there is provided a method of treating amyotrophic lateral sclerosis (ALS) in a human subject in need thereof, the method comprising repetitively intravenously (IV) administering to the subject 1.7-5 mg/kg of a peptide comprising an amino acid sequence as set forth in SEQ ID NO: 1 in a dose escalating manner, thereby treating the ALS in the subject.

According to another aspect of the present invention, there is provided a peptide comprising an amino acid sequence as set forth in SEQ ID NO: 1 for use in treating amyotrophic lateral sclerosis (ALS) in a human subject in need thereof, wherein said peptide is administered to said subject repetitively intravenously (IV) in a dose escalating manner comprising 1.7-5 mg/kg of said peptide.

According to another aspect of the present invention, there is provided a use of a peptide comprising an amino acid sequence as set forth in SEQ ID NO: 1 in the manufacture of a medicament for intravenous (IV) administration for treating amyotrophic lateral sclerosis (ALS) in a human subject in need thereof, wherein said medicament is administered to said subject repetitively in a dose escalating manner comprising 1.7-5 mg/kg of said peptide.

As used herein, the term "treating" refers to inhibiting, preventing or arresting the development of a pathology (i.e. ALS) and/or causing the reduction, remission, or regression of a pathology. Those of skill in the art will understand that various methodologies and assays can be used to assess the development of a pathology or reduction, remission or regression of a pathology, as further disclosed herein.

Amyotrophic lateral sclerosis (ALS), also known as Lou Gehrig's disease and Motor Neuron Disease (MND), is a progressive, fatal, neurodegenerative disease caused by the degeneration of motor neurons, the nerve cells in the central nervous system that control voluntary muscle movement. ALS typically causes muscle weakness and atrophy throughout the body as both the upper and lower motor neurons degenerate, ceasing to send messages to muscles. Unable to function, the muscles gradually weaken, develop fasciculations (twitches) because of denervation, and eventually atrophy because of that denervation. Affected subjects may ultimately lose the ability to initiate and control all voluntary movement; bladder and bowel sphincters and the muscles responsible for eye movement are usually, but not always, spared. Cognitive or behavioral dysfunction is also associated with the disease; about half of ALS subjects experience mild changes in cognition and behavior, and 10-15% show signs of frontotemporal dementia, Language dysfunction, executive dysfunction, and troubles with social cognition and verbal memory are the most commonly reported cognitive symptoms in ALS.

The term "ALS", as used herein, includes all of the classifications of ALS known in the art, including, but not limited to classical ALS (typically affecting both lower and upper motor neurons), Primary Lateral Sclerosis (PLS, typically affecting only the upper motor neurons), Progressive Bulbar Palsy (PBP or Bulbar Onset, a version of ALS that typically begins with difficulties swallowing, chewing and speaking) and Progressive Muscular Atrophy (PMA, typically affecting only the lower motor neurons).

According to specific embodiments, ALS is classical ALS.

The term "ALS" includes sporadic and familial (hereditary) ALS, ALS at any rate of progression (i.e. rapid, non-slow or slow progression) and ALS at any stage (e.g. prior to onset, at onset and late stages of ALS).

According to specific embodiments, ALS is sporadic ALS.

According to specific embodiments, ALS is familial ALS.

According to specific embodiments, ALS is rapid progression ALS.

As used herein, the phrase "rapid progression ALS" refers to ALS in which the symptoms progress continuously and significant degradation of motor neurons can be observed within less than a year with subject survival of up to 4 years from diagnosis.

According to specific embodiments, the rapid progression ALS is characterized by a change of above 0.65 ALSFRS-R points over a period of 1 month.

According to specific embodiments, ALS is non-slow progression ALS.

As used herein, the phrase "non-slow progression ALS" refers to ALS with subject survival of up to 5 years from diagnosis. According to specific embodiments, the non-slow progression ALS is characterized by a change of above 0.55 ALSFRS-R points over a period of 1 month.

According to specific embodiments, ALS is ALS-associated depression.

As used herein, the phrase "ALS-associated depression" refers to depression and/or anxiety which begin following ALS onset. According to specific embodiments, the ALS-associated depression is part of the ALS mechanism of action and may be attributed to e.g. Pseudo Bulbar Affect and frontal lobe dementia. Methods of diagnosing and monitoring depression are well known in the art and include, but not limited to, the ALS Depression Inventory (ADI-12), the Beck Depression Inventory (BDI); and the Hospital Anxiety Depression Scale (HADS) questionnaires.

As mentioned above, the method of the invention is directed, inter alfa, to treating ALS. The treatment may be initiated at any stage of the disease, including following detection of ALS symptoms.

Detection of ALS may be determined by the appearance of different symptoms depending on which motor neurons in the body are damaged first (and consequently which muscles in the body are damaged first). In general, ALS symptoms include the earliest symptoms which are typically obvious weakness and/or muscle atrophy. Other symptoms include muscle fasciculation (twitching), cramping, or stiffness of affected muscles, muscle weakness affecting an arm or a leg and/or slurred and nasal speech. Most ALS patients experience first symptoms in the arms or legs. Others first notice difficulty in speaking clearly or swallowing. Other symptoms include difficulty in swallowing, loss of tongue mobility and respiratory difficulties.

The symptoms may be also classified by the part of neuronal system that is degenerated, namely, upper motor neurons and lower motor neurons. Symptoms of upper motor neuron degeneration include tight and stiff muscles (spasticity) and exaggerated reflexes (hyperreflexia) including an overactive gag reflex. Symptoms of lower motor neuron degeneration include muscle weakness and atrophy, muscle cramps, and fleeting twitches of muscles that can be seen under the skin (fasciculations). To be diagnosed with ALS, patients must have signs and symptoms of upper and/or lower motor neuron damage that cannot be attributed to other causes.

Alternatively, treatment may be initiated at progressive stages of the disease, e.g. when muscle weakness and atrophy spread to different parts of the body and the subject has increasing problems with moving [e.g. the subject may suffer from tight and stiff muscles (spasticity), from exaggerated reflexes (hyperreflexia), from muscle weakness and atrophy, from muscle cramps, and/or from fleeting twitches of muscles that can be seen under the skin (fasciculations)], swallowing (dysphagia), speaking or forming words (dysarthria).

Method of monitoring ALS progression are well known in the art and are further described in the Examples section which follows. Non-limiting examples of such methods include Physical evaluation by a physician; Weight; Electrocardiogram (ECG); ALS Functional Rating Scale (ALSFRS or ALSFRS-R) score; respiratory function which can be measured by e.g. vital capacity (forced vital capacity or slow vital capacity); muscle strength which can be measured by e.g. hand held dynamometry (HHD), hand grip strength dynamometry, manual muscle testing (MMT), electrical impedance myography (EIM) and Maximum Voluntary Isometric Contraction Testing (MVICT); motor unit number estimation (MUNE); cognitive/behavior function which can be measured by e.g. the ALS Depression Inventory (ADI-12), the Beck Depression Inventory (BDI) and the Hospital Anxiety Depression Scale (HADS) questionnaires; Quality of life which can be evaluated by e.g. the ALS Assessment Questionnaire (ALSAQ-40); speech analysis; and Akt level, Akt phosphorylation and/or pAkt:tAkt ratio (see International Patent Application Publication No. WO2012/160563, the contents of which are fully incorporated herein by reference).

According to specific embodiments, the subject is monitored by ALS Functional Rating Scale (ALSFRS); respiratory function; muscle strength and/or cognitive function.

According to specific embodiments, muscle strength is evaluated by a method selected from the group consisting of hand held dynamometry (HHD), hand grip strength dynamometry, manual muscle testing (MMT) and electrical impedance myography (ELM); each possibility represents a separate embodiment of the present invention.

According to specific embodiments, muscle strength is evaluated by a method selected from the group consisting of hand held dynamometry (HHD), hand grip strength dynamometry and electrical impedance myography (UM); each possibility represents a separate embodiment of the present invention.

As used herein the term “subject” refers to a human subject at any age and of any gender which is diagnosed with a disease (i.e., ALS) or is at risk of to develop a disease (i.e. ALS).

According to specific embodiments, the subject has rapid progression ALS and/or ALS-associated depression.

According to specific embodiments the subject fulfills the El Escorial criteria for probable and definite ALS, i.e. the subject presents:

1. Signs of lower motor neuron (LMN) degeneration by clinical, electrophysiological or neuropathologic examination,
2. Signs of upper motor neuron (UMN) degeneration by clinical examination, and
3. Progressive spread of signs within a region or to other regions, together with the absence of:
   Electrophysiological evidence of other disease processes that might explain the signs of LMN and/or UMN degenerations; and
   Neuroimaging evidence of other disease processes that might explain the observed clinical and electrophysiological signs.

According to specific embodiments, the subject has an ALSFRS-R score of >20 prior to treatment according to some embodiments of the present invention.

According to specific embodiments, the subject has an ALSFRS-R score of ≤42 prior to treatment according to some embodiments of the present invention.

According to specific embodiments, the subject has an ALSFRS-R score of 26-42 prior to treatment according to some embodiments of the present invention.

According to specific embodiments, the subject has an ALSFRS-R score of 20-42 prior to treatment according to some embodiments of the present invention.

According to specific embodiments, the subject has a disease progression rate greater than 0.65 ALSFRS-R points per month over the last 3-12 months prior to treatment according to some embodiments of the present invention.

According to specific embodiments, the subject has a disease progression rate greater than 0.55 ALSFRS-R points per month over the last 3-12 months prior to treatment according to some embodiments of the present invention.

According to specific embodiments, the subject has a disease progression rate greater than 0.55 ALSFRS-R points per month within the last 4 months prior to treatment according to some embodiments of the present invention.

According to specific embodiments, the subject has a decline of at least 3 points in ALSFRS-R score within the last 3-12 months prior to treatment according to some embodiments of the present invention.

According to specific embodiments, the subject has a decline of at least 3 points in ALSFRS-R score within the last 4 months prior to treatment according to some embodiments of the present invention. According to specific embodiments, the subject is between 18-80 years of age.

According to specific embodiments, the subject is between 18-75, between 30-75, between 40-75, between 40-60, between 18-50 or between 30-50 years of age.

According to a specific embodiment, the subject is between 18-75 years of age.

According to specific embodiments, the subject weighs at least 50 kg.

According to specific embodiments, the subject weighs no more than 100 kg.

According to specific embodiments, the subject has a BMI between 18.5-30 or between 18.5-25 kg/$m^2$.

According to specific embodiments, the subject is treated with a stable dose of riluzole or edaravone for at least 30 days prior to treatment according to some embodiments of the present invention.

According to specific embodiments, the subject is not a pregnant or lactating female subject.

According to specific embodiments, the subject has no psychiatric disorder.

According to specific embodiments, the subject has no psychiatric disorder which started before ALS onset.

According to specific embodiments, the psychiatric disorder does not include a depression (which was diagnosed before the ALS) and/or anxiety disorder.

According to specific embodiments, the subject does not use a tracheostomy, tracheostomy invasive mechanical ventilation (TIMV).

According to specific embodiments, the subject is not afflicted with active infection.

According to specific embodiments, the subject does not have a history of HIV, positive HBV or HCV serology.

According to specific embodiments, the subject does not have cancer.

As used herein, the phrase "peptide comprising an amino acid sequence as set forth in SEQ ID NO: 1" refers to IPL344 SEQ ID NO: 1, also known as Stressin-1) peptide (see International Patent Application Publication Nos: WO2006/021954 and WO2012/160563, the contents of which are fully incorporated herein by reference).

In an embodiment, the peptide has an amino acid sequence as set forth in SEQ ID NO: 1.

According to a specific embodiment, the peptide is as set forth in SEQ ID NO: 1.

According to a specific embodiment, the peptide consists of SEQ ID NO: 1.

According to other specific embodiments of the invention, the peptide is attached to a non-proteinaceous moiety.

According to specific embodiments, the isolated peptide and the attached non-proteinaceous moiety are covalently attached, directly or through a spacer or a linker.

The phrase "non-proteinaceous moiety" as used herein refers to a molecule not including peptide bonded amino acids that is attached to the above-described peptide.

According to a specific embodiment the non-proteinaceous is a non-toxic moiety. Exemplary non-proteinaceous moieties which may be used according to the present teachings include, but are not limited to a drug, a chemical, a small molecule, a polynucleotide, a detectable moiety, polyethylene glycol (PEG), Polyvinyl pyrrolidone (PVP), poly (styrene comaleic anhydride) (SMA), and divinyl ether and maleic anhydride copolymer (DIVEMA). According to specific embodiments of the invention, the non-proteinaceous moiety comprises polyethylene glycol (PEG).

The peptides of some embodiments of the invention may be synthesized by any techniques that are known to those skilled in the art of peptide synthesis, such as, but not limited to, solid phase and recombinant techniques.

According to specific embodiments, the peptide is synthesized by solid phase. For solid phase peptide synthesis, a summary of the many techniques may be found in J. M. Stewart and J. D. Young, Solid Phase Peptide Synthesis, W. H. Freeman Co. (San Francisco), 1963 and J. Meienhofer, Hormonal Proteins and Peptides, vol. 2, p. 46, Academic Press York), 1973. For classical solution synthesis see G. Schroder and K. Lupke, The Peptides, vol. 1, Academic Press (New York), 1965.

In general, these methods comprise the sequential addition of one or more amino acids or suitably protected amino acids to a growing peptide chain. Normally, either the amino or carboxyl group of the first amino acid is protected by a suitable protecting group. The protected or derivatized amino acid can then either be attached to an inert solid support or utilized in solution by adding the next amino acid in the sequence having the complimentary (amino or carboxyl) group suitably protected, under conditions suitable for forming the amide linkage. The protecting group is then removed from this newly added amino acid residue and the next amino acid (suitably protected) is then added, and so forth. After all the desired amino acids have been linked in the proper sequence, any remaining protecting groups (and any solid support) are removed sequentially or concurrently, to afford the final peptide compound. By simple modification of this general procedure, it is possible to add more than one amino acid at a time to a growing chain, for example, by coupling (under conditions which do not racemize chiral centers) a protected tripeptide with a properly protected dipeptide to form, after deprotection, a pentapeptide and so forth. Further description of peptide synthesis is disclosed in U.S. Pat. No. 6,472,505.

A preferred method of preparing the peptide compounds of some embodiments of the invention involves solid phase peptide synthesis.

Large scale peptide synthesis is described by Andersson Biopolymers 2000; 55(3):227-50.

Since the peptides of the present invention are utilized in-vivo, the peptide, medicament and compositions comprising same are of high purity and substantially free of potentially harmful contaminants, e.g., at least GMP grade, at least pharmaceutical grade. To the extent that a given compound must be synthesized prior to use, such synthesis or subsequent purification shall preferably result in a product that is substantially free of any potentially contaminating toxic agents that may have been used during the synthesis or purification procedures.

The peptide of some embodiments of the invention can be administered to an organism per se, or in a pharmaceutical composition where it is mixed with suitable carriers or excipients.

As used herein a "pharmaceutical composition" refers to a preparation comprising the peptide of the invention (i.e. the active ingredient) with other chemical components such as physiologically suitable carriers and excipients. The purpose of a pharmaceutical composition is to facilitate administration of a compound to an organism.

Hereinafter, the phrases "physiologically acceptable carrier" and "pharmaceutically acceptable carrier" which may be interchangeably used refer to a carrier or a diluent that does not cause significant irritation to an organism and does not abrogate the biological activity and properties of the administered compound. An adjuvant is included under these phrases.

Herein the term "excipient" refers to an inert substance added to a pharmaceutical composition to further facilitate administration of the peptide (i.e. the active ingredient). Examples, without limitation, of excipients include calcium carbonate, calcium phosphate, various sugars and types of starch, cellulose derivatives, gelatin, vegetable oils and polyethylene glycols.

Techniques for formulation and administration of drugs may be found in "Remington's Pharmaceutical Sciences," Mack Publishing Co., Easton, PA, latest edition, which is incorporated herein by reference.

According to specific embodiments, the peptide used in the methods and compositions of the present invention is formulated in a composition comprising 2.5-8% peptide, 2.5-6% peptide, 2.5-5.5% peptide, 3-8% peptide, 3-6% peptide, 3-5.5% peptide, 4-8% peptide, 4-6% peptide or 4.5-5.5% peptide, each possibility represents a separate embodiment of the present invention.

According to specific embodiments, the peptide used in the methods and compositions of the present invention is formulated in a composition comprising 5% peptide.

According to specific embodiments, a composition comprising the peptide has a pH>4.

According to specific embodiments, a composition comprising the peptide has a pH of 4.1-6, 4.2-5.8, 4.2-5.6, 4.2-5.5, 4.3-5.5, 4.5-5.5, 4.5-5, 5-5.5, 5.5-6 or 4.3-4.4, each possibility represents a separate embodiment of the present invention.

According to specific embodiments, a composition comprising the peptide has a pH of 4.5-5.5.

Thus, according to an aspect of the present invention, there is provided a composition comprising 5% peptide comprising an amino acid sequence as set forth in SEQ ID NO: 1, wherein the composition has a pH of 4.5-5.5.

According to specific embodiments, a composition comprising the peptide comprises PBS and/or dPBS.

As used herein "PBS (phosphate buffered saline)" and "dPBS (Dulbecco's phosphate buffered saline)" refers to a water based salt solution containing sodium hydrogen phosphate, sodium chloride and, in some formulation, potassium chloride and potassium dihydrogen phosphate with isotonic osmolality and ion concentration. dPBS has a lower phosphate concentration than PBS and typically contains 8.1 mM $Na_2HPO_4$, wherein PBS contains 10 mM $Na_2HPO_4$.

According to specific embodiments, the PBS and/or dPBS comprise calcium and magnesium.

Typically, calcium ($CaCl_2$) and magnesium ($MgCl_2$) concentrations in PBS or dPBS are 0.9 mM and 0.5 mM, respectively.

PBS and dPBS can be produced by methods well known in the art and disclosed e.g. in Sambrook, Fritsch, and Maniatis (1989) Molecular Cloning: A Laboratory Manual, 2nd ed., Cold Spring Harbor Laboratory Press, Cold Spring Harbor, New York, volume 3, appendix B.12; and Dulbecco, R.; et al. (1954). J. Exp. Med. 99 (2): 167-182. Alternatively or additionally, PBS and dPBS are commercially available from e.g. Gibco, Sigma-Aldrich, Biological industries and Thermo Fisher Scientific.

According to specific embodiments, a composition comprising the peptide comprises saline.

Suitable routes of administration may, for example, include intramuscular, subcutaneous and intramedullary injections as well as intrathecal, intravenous, direct intraventricular, intracardiac, e.g., into the right or left ventricular cavity and into the common coronary artery.

According to specific embodiments, the peptide, the medicament or the composition comprising same is administered intravenously (IV).

According to specific embodiments, the peptide the medicament or the composition comprising same is administered to the subject by a cannula, a peripherally inserted central catheter (PICC) line or central venous port or catheter (CVC) such as Hickman.

Alternately, one may administer the pharmaceutical composition in a local rather than systemic manner, for example, via injection of the pharmaceutical composition directly into a tissue region of a patient.

Compositions of some embodiments of the invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with some embodiments of the invention thus may be formulated in conventional manner using one or more physiologically acceptable carriers comprising excipients and auxiliaries, which facilitate processing of the active ingredients into preparations which, can be used pharmaceutically. Proper formulation is dependent upon the route of administration chosen.

For injection, the peptides of the pharmaceutical composition may be formulated in aqueous solutions, preferably in physiologically compatible buffers such as Hank's solution, Ringer's solution, or physiological salt buffer.

According to specific embodiments, the peptide, the medicament or the composition comprising same described herein are formulated for parenteral (e.g. intravenous) administration, e.g., by bolus injection or continuous infusion.

According to specific embodiments, the peptide, the medicament or the composition comprising same is administered by bolus injection.

According to specific embodiments, the peptide, the medicament or the composition comprising same is administered by IV infusion.

According to specific embodiments, the peptide, the medicament or the composition comprising same is administered within minutes using an electronic infusion pump; e.g. over a time period of 1-5 minutes.

According to specific embodiments, the peptide, the medicament or the composition comprising same is administered using an electronic infusion pump with a flow rate of 20-400 ml/hour, 100-350 ml/hour, 100-300 ml/hour, 150-350 ml/hour, 150-300 ml/hour or 100-200 ml/hour.

According to specific embodiments, the IV infusion is a fast dripping IV infusion, e.g. over a time period of less than 30 minutes, e.g. over a time period of less than 10 minutes, e.g. over a time period of about 5 minutes.

According to other specific embodiments, the IV infusion is a slow dripping IV infusion e.g. over a time period of more than 30 minutes.

According to specific embodiments, the compositions may be suspensions, solutions or emulsions in oily or aqueous vehicles.

Compositions for parenteral administration include aqueous solutions of the active preparation in water-soluble form. Additionally, suspensions of the peptides may be prepared as appropriate oily or water based injection suspensions. Suitable lipophilic solvents or vehicles include fatty oils such as sesame oil, or synthetic fatty acids esters such as ethyl oleate, triglycerides or liposomes. Aqueous injection suspensions may contain substances, which increase the viscosity of the suspension, such as sodium carboxymethyl cellulose, sorbitol or dextran. Optionally, the suspension may also contain suitable stabilizers or agents, which increase the solubility of the peptides to allow for the preparation of highly concentrated solutions.

Alternatively, the active composition may be in powder form for constitution with a suitable vehicle, e.g., sterile, pyrogen-free water based solution, before use.

Thus, according to other specific embodiments, the composition is extractable (i.e. lyophilized).

The compositions may also contain formulatory agents such as suspending, stabilizing and/or dispersing agents.

Formulations comprising the peptide disclosed herein may be presented as a unit dosage form, e.g., in ampoules or in multi-dose containers with optionally, an added preservative. In such form, the preparation is subdivided into unit doses containing appropriate quantities of the peptide, such as for a single administration, which allow for effective concentration of the peptide as further disclosed herein (e.g. 2-5 mg/kg, 2.5-4.5 mg/kg, 3-4 mg/kg, 2.8-3.8 mg/kg, 2.9-3.7 mg/kg, 3-3.5 mg/kg, 3-3.4 mg/kg, about 3.2 mg/kg or about 4.5 mg/kg). The unit dosage form can be a packaged preparation, the package containing discrete quantities of preparation, for example, a glass vial.

Thus, according to an aspect of the present invention, there is provided a unit dosage form comprising 140-350 mg peptide comprising an amino acid sequence as set forth in SEQ ID NO: 1 formulated for intravenous (IV) administration.

According to specific embodiments, the unit dosage form comprises 140-315 mg peptide.

According to specific embodiments, the unit dosage form comprises 210-280 mg peptide.

According to specific embodiments, the unit dosage form comprises 200-270 mg peptide.

According to specific embodiments, the unit dosage form comprises 220-250 mg peptide.

According to specific embodiments, the unit dosage form comprises about 22 mg peptide.

According to specific embodiments, the unit dosage form comprises 315-345 mg peptide.

According to specific embodiments, the unit dosage form comprises about 315 mg peptide.

The quantity of a unit dose of preparation administered to a subject may be varied or adjusted according to subject's weight. Hence unit dosage forms encompassed by the present invention comprise also unit doses with lower quantities of the peptide wherein 2-4 unit dosages are administered to the subject according to the subject's weight to allow an effective concentration of the peptide as further disclosed herein (e.g. 2-5 mg/kg, 2.5-4.5 mg/kg, 3-4 mg/kg, 2.8-3.8 mg/kg, 2.9-3.7 mg/kg, 3-3.5 mg/kg, 3-3.4 mg/kg, about 3.2 mg/kg or about 4.5 mg/kg).

Thus, according to another aspect of the present invention there is provided a unit dosage form comprising 35-90 mg peptide comprising an amino acid sequence as set forth in SEQ ID NO: 1 formulated for intravenous (IV) administration.

According to specific embodiments, the unit dosage form comprises 35-80 mg peptide.

According to specific embodiments, the unit dosage form comprises 50-70 mg peptide.

According to specific embodiments, the unit dosage form comprises 50-65 mg peptide.

According to specific embodiments, the unit dosage form comprises 55-65 mg peptide.

According to specific embodiments, the unit dosage form comprises about 60 mg peptide.

According to specific embodiments, the unit dosage form comprises 75-90 mg peptide.

According to specific embodiments, the unit dosage form comprises about 80 mg peptide.

Compositions suitable for use in context of some embodiments of the invention include compositions wherein the peptide of the present invention is contained in an amount effective to achieve the intended purpose. More specifically, a therapeutically effective amount means an amount of peptide effective to prevent, alleviate or ameliorate symptoms of a disorder (i.e., ALS) or prolong the survival of the subject being treated.

According to specific embodiments, the peptide, the medicament or the composition comprising same is administered at a dose comprising 2-5 mg/kg peptide.

According to specific embodiments, the peptide, the medicament or the composition comprising same is administered at a dose comprising 2.2-4.5 mg/kg peptide.

According to specific embodiments, the peptide, the medicament or the composition comprising same is administered at a dose comprising 2.5-4.5 mg/kg peptide.

According to specific embodiments, the peptide, the medicament or the composition comprising same is administered at a dose comprising 2.7-4.5 mg/kg peptide.

According to specific embodiments, the peptide, the medicament or the composition comprising same is administered at a dose comprising 2.5-4 mg/kg peptide.

According to specific embodiments, the peptide, the medicament or the composition comprising same is administered at a dose comprising 2.2-3.5 mg/kg peptide.

According to specific embodiments, the peptide, the medicament or the composition comprising same is administered at a dose comprising 3-4 mg/kg peptide.

According to specific embodiments, the peptide, the medicament or the composition comprising same is administered at a dose comprising 2.8-3.8 mg/kg peptide.

According to specific embodiments, the peptide, the medicament or the composition comprising same is administered at a dose comprising 2.9-3.7 mg/kg peptide.

According to specific embodiments, the peptide, the medicament or the composition comprising same is administered at a dose comprising 3-3.5 mg/kg peptide.

According to specific embodiments, the peptide, the medicament or the composition comprising same is administered at a dose comprising 3-3.4 mg/kg peptide.

According to specific embodiments, the peptide, the medicament or the composition comprising same is administered at a dose comprising about 3.2 mg/kg peptide.

According to specific embodiments, the peptide, the medicament or the composition comprising same is administered at a dose comprising about 3.5 mg/kg peptide.

According to specific embodiments, the peptide, the medicament or the composition comprising same is administered at a dose comprising 3.2-3.5 mg/kg peptide.

According to specific embodiments, the peptide, the medicament or the composition comprising same is administered at a dose comprising 3.2 mg/kg peptide.

According to specific embodiments, the peptide, the medicament or the composition comprising same is administered at a dose comprising 3.5 mg/kg peptide.

According to specific embodiments, the peptide, the medicament or the composition comprising same is administered at a dose comprising about 4.5 mg/kg peptide.

According to specific embodiments, the peptide, the medicament or the composition comprising same is administered at a dose comprising about 4.9 mg/kg peptide.

According to specific embodiments, the peptide, the medicament or the composition comprising same is administered at a dose comprising 4.5-4.9 mg/kg peptide.

According to specific embodiments, the peptide, the medicament or the composition comprising same is administered at a dose comprising 4.5 mg/kg peptide.

According to specific embodiments, the peptide, the medicament or the composition comprising same is administered at a dose comprising 4.9 mg/kg peptide.

The amount of a composition to be administered will, of course, be dependent on the subject being treated, the severity of the affliction, the manner of administration, the judgment of the prescribing physician, etc.

Depending on the severity and responsiveness of the condition to be treated, dosing can be of a single or a plurality of administrations, with course of treatment lasting from several days to several weeks or until cure is effected or diminution of the disease state is achieved.

According to specific embodiments, administration is effected on a daily basis.

According to specific embodiments, administration is effected repetitively in a dose escalating manner.

According to specific embodiments, the dose escalating is by 0.2-1 mg/kg, by 0.2-0.5 mg/kg, 0.3-1 mg/kg, 0.3-0.5 mg/kg or 0.5-1 mg/kg in each step.

According to specific embodiments, the dose escalating is by 0.3-0.5 mg/kg.

According to specific embodiments, the dose escalating is effected every 2-60 days, every 2-30 days, every 2-14 days, 2-10 day, every 2-7 days or every 3-4 days.

According to specific embodiments, the dose escalating is effected every 2-7 days.

According to specific embodiments, dose escalating is stopped when reaching a dose of 5 mg/kg.

According to other specific embodiments, dose escalating it stopped in the event of hypersensitivity or an adverse event (AE) related to the peptide, the medicament or the composition.

Specific embodiments relating to hypersensitivity and AEs and modes of action when encountering them are described in Examples 1-2 hereinbelow which is to be understood as forming an integral part of the present section.

According to specific embodiments, in the event of an AE related to the peptide, the medicament or the composition (e.g. AEs which are ≥Grade 3 toxicity) the dose is reduced to the previous administered dose which is not accompanied by the AE.

According to specific embodiments, in the event of hypersensitivity related to the peptide, the medicament or the composition [evidenced by e.g. sinus tachycardia, heavy breathing or rash (along the veins or elsewhere)], the peptide, the medicament or the composition is administered by a desensitization procedure.

According to specific embodiments, desensitization is effected by slow dripping IV infusion at the last administered dose.

According to specific embodiments, following desensitization, dose escalating is continued.

Peptides and compositions of some embodiments of the invention may, if desired, be presented in a pack or dispenser device, such as an FDA approved kit, which may contain one or more unit dosage forms containing the peptide. The pack may, for example, comprise metal or plastic foil, such as a blister pack. According to specific embodiments, the composition is packaged in a glass vial, so as to prevent adherence of the peptide to the vial. The pack or dispenser device may be accompanied by instructions for administration. The pack or dispenser may also be accommodated by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert. Compositions comprising a preparation of the invention formulated in a compatible pharmaceutical carrier may also be prepared, placed in an appropriate container, and labeled for treatment of an indicated condition, as is further detailed above.

The present invention further contemplates administration of other therapeutic drugs to the subject. Exemplary drugs which may be administered include, but are not limited to, oxidative agents, non-halogen activated-oxygen compounds, non-oxygen activated-halogen compounds, N-halo compounds, riluzole and edaravone.

As used herein the term “about” refers to ±10%.

The terms “comprises”, “comprising”, “includes”, “including”, “having” and their conjugates mean “including but not limited to”.

The term “consisting of” means “including and limited to”.

The term “consisting essentially of” means that the composition, method or structure may include additional ingredients, steps and/or parts, hut only if the additional ingredients, steps and/or parts do not materially alter the basic and novel characteristics of the claimed composition, method or structure.

As used herein, the singular form “a”, “an” and “the” include plural references unless the context clearly dictates otherwise. For example, the term “a compound” or “at least one compound” may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range, The phrases “ranging/ranges between” a first indicate number and a second indicate number and “ranging/ranges from” a first indicate number “to” a second indicate number are used herein interchangeably and are meant to include the first and second indicated numbers and all the fractional and integral numerals therebetween.

As used herein the term “method” refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

When reference is made to particular sequence listings, such reference is to be understood to also encompass sequences that substantially correspond to its complementary sequence as including minor sequence variations, resulting from, e.g., sequencing errors, cloning errors, or other alterations resulting in base substitution, base deletion or base addition, provided that the frequency of such variations is less than 1 in 50 nucleotides, alternatively, less than 1 in 100 nucleotides, alternatively, less than 1 in 200 nucleotides, alternatively, less than 1 in 500 nucleotides, alternatively, less than 1 in 1000 nucleotides, alternatively, less than 1 in 5,000 nucleotides, alternatively, less than 1 in 10,000 nucleotides.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes 1411 Ausubel, R. M., ed. (1994); Ausubel et al., "Current Protocols in Molecular Biology", John Wiley and Sons, Baltimore, Maryland (1989); Perbal, "A Practical Guide to Molecular Cloning", John Wiley & Sons, New York (1988); Watson et al., "Recombinant DNA", Scientific American. Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Culture of Animal Cells—A Manual of Basic Technique" by Freshney, Wiley-Liss, N. Y. (1994), Third Edition; "Current Protocols in Immunology" Volumes I-III Coligan J. E., ed. (1994); Stites et al. (eds), "Basic and Clinical Immunology" (8th Edition), Appleton & Lange, Norwalk, CT (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds, (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol, 1-317, Academic Press; "PCR Protocols: A Guide To Methods And Applications", Academic Press, San Diego, CA (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Example 1

Materials and Methods

IPL344 formulation and dosage—IPL344, 7 amino acids synthetic peptide [LPPLPYP (SEQ ID NO: 1), referred to herein is base peptide] is formulated in aqueous solution [peptide dissolved in dPBS (with Ca++ and Mg++] at a concentration of 50 mg/ml (i.e. 5%, base peptide, not including acetate and impurities). Peptide concentration is determined by absorbance at 280 nm (A280, Thermo Fisher Scientific) minus impurities as identified upon drug substance (DS) release by HPLC.

Drug product (DP) is supplied in glass vials, 1.4-1.5 ml per vial (extractable), to be stored at 5±3° C. Stability studies of the DP filled in single use glass vials, indicate that the DP can be stored at 5±3° C. for up to at least 18 months.

IPL344 is administered intravenously (IV) once daily, delivered by a cannula, a peripherally inserted central catheters (PICC) line or central venous port or catheter (CVC) such as Hickman port; as a bolus, using an electronic infusion pump, or by rapid infusion of the drug diluted in 50 ml saline.

Dose-limiting Toxicity (DLT): DLT is defined as a ≥Grade 3 per subject which is IPL344 drug-related adverse event (using CTCAE Version v.4.03) occurring at any dosing, excluding:

- Grade 3 adverse event of hypersensitivity (defined as sinus tachycardia, heavy breathing or rash along the veins or elsewhere)
- A transient (resolving within 6 hours of onset) Grade 3 study drug-related adverse event.

A DLT is considered related to IPL344 unless there is a clear, well-documented, alternative explanation for the toxicity.

Dose Adjustments, Infusion Delays, and Missed Doses—Dose escalations or de-escalations are permitted within each subject's treatment (as detailed for example in Table 3 hereinbelow). Dose adjustments are allowed, for example, if the subject experiences a DLT or a hypersensitivity reaction.

In cases of missed doses, typically, if the delay is 1 day, the procedures are performed according to the original scheduled visit. In the case that an injection or infusion cannot be administered at a scheduled visit, it is administered as soon as possible.

Adverse events (AE)—The FDA defines an AE as "any untoward medical occurrence associated with the use of a drug in humans, whether or not considered drug related" (US Department of Health and Human Services, December 2012). Medical conditions present before first administration of IPL344 are considered pre-existing conditions and are documented as medical history. A new condition, event or the worsening of a pre-existing condition is considered an AE from the first dose of administration.

Each AE is assessed with regard to seriousness, severity, and relation to the treatment, as shown in Tables 1-2 below. AEs are coded by CTCAE Version v4.03.

TABLE 1

Definition of adverse events intensity

| INTENSITY | DEFINITION |
|---|---|
| MILD | A mild AE is one where the symptoms are barely noticeable to the participant. It does not influence the performance or prevent the participant from carrying on with normal life activities. |

TABLE 1-continued

| Definition of adverse events intensity | |
|---|---|
| INTENSITY | DEFINITION |
| MOD-ERATE | A moderate AE is one where the symptoms make a participant uncomfortable and cause some impairment to normal life activities. Treatment for symptom(s) may be required. |
| SEVERE | A severe AE is one where the symptoms cause severe discomfort to the participant and severely limit the participant's normal daily activities. Treatment for symptom(s) is given. Note that serious and severe are not synonymous. |

Vital Signs—Vital signs include blood pressure, heart rate, oral temperature, respiration rate and pulse oximetry measurements. Vital signs can be measured as specified e.g. in the Schedule of Assessments (Table 3 below): These measurements are taken before any administration and 15-20 minutes, 1 hour and 4 hours post administration. For visits conducted at home, measurements are taken before any administration and 15-20 minutes and 1-hour post administration.

Physical evaluation—a physical examination including general ambulation status is carried out by a study physician as specified e.g. in the Schedule of Assessments (Table 3 below). The physical examination includes appearance, eyes, ears, nose, head, throat, neck, chest, lungs, heart, abdomen, extremities, skin, and musculoskeletal system. Additional examination is performed as found relevant by the investigator/physician.

TABLE 2

| Definition of relationship of adverse events to the investigational product | | |
|---|---|---|
| TERM | DEFINITION | CLARIFICATION |
| Unrelated | In general, this category can be considered applicable to those AES, which after careful medical consideration at the time they are evaluated, are judged to be unrelated to the test drug. | An AE may be considered unlikely related if or when (must have two):<br>It does not follow a reasonable temporal sequence from the administration of the test drug.<br>It could readily have been produced by the participant's clinical state, environmental or toxic factors, or other modes of therapy administered to the participant.<br>It does not follow a known pattern of response to the test drug.<br>It does not reappear or worsen when the drug is re-administered. |
| Possibly Related | This category applies to those AEs for which, after careful medical consideration at the time they are evaluated, a connection with the test drug administration appears unlikely but cannot be ruled out with certainty. | An AE may be considered possibly related if or when (at least two of the following):<br>It follows a reasonable temporal sequence from administration of the drug.<br>It could not readily have been produced by the participant's clinical state, environmental or toxic factors, or other modes of therapy administered to the participant.<br>It follows a known pattern of response to the test drug. |
| Probably Related | This category applies to those AEs which, after careful medical consideration at the time they are evaluated, are felt with a high degree of certainty to be related to the test drug. | An AE may be considered probably related if or when (at least three of the following):<br>It follows a reasonable temporal sequence from administration of the drug.<br>It could not be reasonably explained by the known characteristics of the participant's clinical state, environmental or toxic factors or other modes of therapy administered to the participant.<br>It disappears or decreases on cessation or reduction in dose. There are important exceptions when an adverse event does not disappear upon discontinuation of the drug, yet drug-relatedness clearly exists.<br>It follows a known pattern of response to the test drug. |

Serious adverse events (SAE)—An SAE is any AE occurring at any IPPL344 dose that suggests a significant hazard or side effect, regardless on the relationship to IPPL344 and that results in, but may not be limited to, any of the following outcomes:

death (regardless of the cause);

a life-threatening adverse event or suspected adverse reaction;

if participant is hospitalized or prolongation of existing hospitalization associated with a clinical AE (any participant hospital admission that includes a minimum of an overnight stay in a health care facility);

a persistent or significant disability/incapacity or a substantial disruption of the ability to conduct normal life functions;

a congenital anomaly or birth defect.

Important medical events that may not result in death, be life-threatening, or require hospitalization may be serious when, based upon appropriate medical judgment, they may jeopardize the participant and may require medical or surgical intervention to prevent one of the outcomes listed above.

Electrocardiogram (ECG)—A 12-lead ECG is recorded as specified e.g. in the Schedule of Assessments (Table 3 below): During treatment period ECG is taken before any IPL344 dose escalation administration and 15-20 minutes, 1 and 4 hours post administration.

Laboratory Assessments—All routine clinical laboratory assessments are performed by the center local laboratory. Safety laboratory tests are carried out as specified e.g. in the Schedule of Assessments (Table 3 below), including:

1. Haematology: Red Blood Cell Count, Haemoglobin (HGB), Hematocrit (HCT), Mean Cell Haemoglobin (MCH), Mean Cell Haemoglobin Concentration (MCHC), Mean Corpuscular Volume (MCV), White Blood Cell (WBC) Count and Differential, Platelet Count and PT/INR.
2. Biochemistry: Total Protein, Albumin, Total bilirubin, Alanine Aminotransferase (ALT), Aspartate Aminotransferase (AST), gamma Glutamyl Transferase (GGT), Lactate Dehydrogenase (LDH), Creatine Phosphokinase (CPK), Alkaline phosphatase, Glucose, Sodium, Potassium, BUN and Creatinine and electrolytes: calcium, potassium, sodium, and chloride.

3. Anti-drug antibodies: blood collection for future testing.
4. Urinalysis (dipstick): Protein, Glucose, Specific Gravity, Ketones, Urobilinogen, Bilirubin, pH, Blood (Haemoglobin) and Leukocytes.

All clinically significant laboratory tests outside the normal range of the site's normal range values are repeated as clinically indicated until the values return to normal, or until the etiology has been determined and the condition considered stable. Abnormal laboratory test results that are considered to be clinically significant as determined by the investigator/physician are reported as an AE. A Laboratory abnormality is not considered an AE unless:

Intervention is required;

Changes in dose are required (decrease, discontinued, interrupted);

Other treatment/therapy is required;

Associated with other diagnoses or medical condition;

Investigator decision after considering the clinical significance of the finding.

Serum Pregnancy Test—Women with child-bearing potential are tested for serum pregnancy using a commercially available kit as specified e.g. in the Schedule of Assessments (Table 3 below).

Weight/Height—Subject is dressed without bulky clothes such as jacket and without shoes. Weight assessment, using a chair scale (Shekel's Multifunction Wheelchair Scale).

Concomitant Medications—Any medications (including prescription, over-the-counter, herbal supplements and health store products) to be taken during treatment are reviewed by a physician. Medications, either prescribed or over-the-counter are checked at each visit and recorded, preferably by their generic name.

Pharmacokinetic (PK)—Blood samples for PK studies are collected at pre-specified time-points: e.g. prior to administration of IPL344 (Time=0) and at 5, 10, 20, 30, 45, 60 and 120 minutes following administration. Approximately 3.0-4.0 mL of whole blood samples are drawn from each subject into plasma tubes with $K_2$EDTA anticoagulant and placed on wet ice, Samples are further processed to plasma within 30 minutes by refrigerated (2 to 8° C.) centrifugation and the supernatant is transferred to four vials (approximately 0.5 mL in 4 aliquots) and stored at −20° C. until further analysis.

Physical strength evaluated by ALSFRS-R score—The Amyotrophic Lateral Sclerosis Functional Rating Scale (ALSFRS) is a validated questionnaire-based scale that measures physical function in carrying out activities of daily living (ADL) of subjects with ALS. The ALSFRS-R provides a physician-generated estimate of the subject's degree of functional impairment, which can be evaluated serially to objectively assess any response to treatment or progression of disease. The components of the scale group into four factors or domains that encompass gross motor tasks, fine motor tasks, bulbar functions and respiratory function. The ALSFRS-R includes 12 questions that ask the examiner to rate his/her impression of the subject's level of functional impairment in performing one of twelve common tasks (speech, salivation, swallowing, handwriting, cutting food and gastronomy capabilities, dressing and hygiene, turning in bed, walking, climbing stairs, dyspnea, orthopnea and respiratory insufficiency). Each task is rated on a five-point scale from 0=cannot do, to 4=normal ability. Individual item scores are summed to produce a reported score of between 0=worst and 48=best.

Respiratory function—evaluated by Slow Vital Capacity (SVC): Vital capacity (VC) that measures the volume of air expired, non-forcefully, in one breath.

Muscle strength—evaluated by:

(a) Hand Held Dynamometry (HHD)/Hand Grip Strength—Dynamometry is a method of strength testing using sophisticated dedicated strength measuring devices (e.g., hand-grip, hand-held dynamometer). In hand grip dynamometer, the curved handle of the dynamometer mimics the pattern of the hand when making a fist. The handle is pliable and receptive to pressure against it. Attached to the Hand grip is a monitor that shows the strength of the squeeze.

And optionally or alternatively:

(b) Manual Muscle Testing (MMT)—Manual muscle testing is a procedure for the evaluation of the function and strength of individual muscles and muscle groups based on the effective performance of a movement in relation to the forces of gravity and manual. MMT scores muscle strength according to whether the muscle can move the lever arm against gravity (3/5-5/5), without gravity (2/5), or demonstrate a palpable contraction (1/5).

Cognitive function—evaluated by depression and/or anxiety evaluation using a questionnaire according to the ALS Depression Inventory (ADI-12), the Beck Depression Inventory (BDI); and/or the Hospital Anxiety Depression Scale (HADS).

Statistical analysis—Statistical analyses is performed using SAS® v9.4 or higher (SAS Institute, Cary NC, USA). Descriptive statistics for continuous variables are provided using the mean, standard deviation and/or standard error of the mean, minimum, maximum, and number of observations. Descriptive statistics for discrete data are provided using frequencies (n) and percentages (%). 95% two-sided confidence intervals are provided where deemed relevant. Baseline values are defined as the last valid value prior to first study drug administration. Baseline for safety parameters is defined as the last available and evaluable parameter value before and closest to the drug administration of each dose-period. If a rechecked value is used for baseline, it is collected under the same conditions as for the planned baseline (e.g., fasting condition). Sample size comprises 8-15 participants.

Safety Analysis: The Safety population is based on participants having received at least one dose of IPL344 (exposed population), including participants prematurely withdrawn. AEs are classified by system-organ class and preferred term and then summarized by number and percentage of participants experiencing AEs. SAE's, study drug related and unrelated AE's, are presented in tabular format by dose; the CTC score is presented by dose. Toxicity scores are presented by grade, dose level, and tabulated separately for observations occurring within 1 hour from administration and other observations. The IPL344 DLT and maximal tolerated dose (MTD) are assessed and presented. Physical examinations, blood and urine tests and vital signs are presented in tabular format by dose.

PK Analysis: Pharmacokinetic analysis is performed for participants with no major deviations related to drug administration (e.g. incomplete infusion of IPL344). Participants with missing plasma sample data in some but not all time points are included in the analysis.

A population PK analysis is followed by Bayesian fitting algorithm to estimate each subject PK characteristics and reconstruction of each individual full PK curve. These individual. PK curves are then used for a subsequent non compartmental analysis (NCA) analysis from which Tmax, Cmax, T-1/2, λz, and AUC(0-t) are determined.

$AUC_{0-t}$: Area under the plasma concentration-time curve from time 0 to the time (t) of last quantifiable concentration (Ct) calculated by the linear trapezoidal rule.

$C_{max}$: The maximum observed plasma concentration.

$T_{max}$: The observed time to reach maximum plasma concentration.

λz: The terminal-phase exponential rate constant as calculated from the negative slope of the regression line for the terminal linear portion of the LN transformed plasma concentration versus time curve.

$T_{1/2}$: The apparent terminal exponential half-life, calculated as ln(2)/λz.

Time-course profiles of individual plasma concentrations of IPL344 following administration of each dose are presented by subject figures including all patients for each dose. Mean (SD) plasma concentrations obtained for each dose level are plotted as well.

The actual sampling times are used for PK analysis (when actual sampling times are not available, theoretical times are used instead).

Calculated pharmacokinetic parameters as described above (AUC, Tmax, Cmax and $T_{1/2}$) are tabulated along with summary statistics, including number of observations, arithmetic and geometric means, SD, coefficient of variation (CV %), median, minimum, and maximum, for each dose.

TABLE 3

Exemplary Detailed Schedule of Assessments for 28 days dose escalation treatment
Schedule of Events

| | | Screening (Visit | Baseline* (Visit | Clinic Visit (Visits 3-6) Treatment *** Dose Escalation | | | | Home Visit | | | | Clinic Visit | Home care Off | Clinic Visit (Visit 8) |
|---|---|---|---|---|---|---|---|---|---|---|---|---|---|---|
| | Pre Screen- | 1) (−28)- | 2) (−7)- | 1** (Visit | 4 (Visit | 7 (Visit | 10 (Visit | Treatment Maintenance | | | | (Visit 7) | IPL344 35, | End of Study |
| Day | ing | (−1) | (−1) | 3) | 4) | 5) | 6) | 2, 3 | 5, 6 | 8, 9 | 11-27 | 28 | 43, 49 | 56 |
| Informed consent | | X | | | | | | | | | | | | |
| Demographics | | X | | | | | | | | | | | | |
| Medical History [a] | X | X | | | | | | | | | | | | |
| Neurological examination of ALSFRS-R | | | X | | | | | | | | | X | | X |
| Slow vital capacity (SVC) | | | X | | | | | | | | | X | | X |
| Forced vital capacity (FVC) | | | X | | | | | | | | | | | |
| HHD, MMT, Hand grip strength | | | X | | | | | | | | | X | | X |
| Prior ALS treatments | | X | | | | | | | | | | | | |
| Depression, anxiety and/or quality of life evaluation | | | X | | | | | | | | | X | | X |
| Physical examination | | X | | X | X | X | X | | | | | X | | X |
| Weight/Height/ BMI [b] | | X[K] | X | | | | | | | | | X | | |
| Vital signs [c] | | X | | X | X | X | X | X | X | X | X | X | | X |
| Serum pregnancy test | | X | | | | | | | | | | | | |
| Coagulation [d] markers | | X | | X | X | X | X | | | | | X | | X |
| Hematology [e] | | X | | X | X | X | X | | | | | X | | X |
| Chemistry [f] | | X | | X | X | X | X | | | | | X | | X |
| Urinanalysis [g] | | X | | X | X | X | X | | | | | X | | X |
| HIV, HBV and HCV serology | | X | | | | | | | | | | | | |
| Cannula, CVC or PICC line or port placement | | | X | | | | | | | | | | | |
| Cannula, CVC or PICC line or port removal [m] | | | | | | | | | | | | X | | |
| 12-lead electro-cardiogram (ECG) [h] | | X | | X | X | X | X | | | | | X | | X |

TABLE 3-continued

Exemplary Detailed Schedule of Assessments for 28 days dose escalation treatment
Schedule of Events

| | | | | | | | | | | | | | |
|---|---|---|---|---|---|---|---|---|---|---|---|---|---|
| IPL344 administration | | | X | X | X | X | X | X | X | X | X | | |
| Nurse Phone FU | | | | | | | | | | | | X | |
| IPL344 self-administration training [i] | | | | | | | | | | X | | | |
| AEs evaluation [j] | | | X | X | X | X | X | X | X | X | X | X | X |
| DLTs | | | X | X | X | X | X | X | X | X | | | |
| Concomitant Medication [k] | X | X | X | X | X | X | X | X | X | X | X | X | X |
| Sample Blood PK[l] | | | X | X | X | X | | | | | X | | |
| Participant Instructions form | | X | | | | | | | | | | | |
| Blood for Anti-drug antibody | | | X | | | | | | | | X | | X |

Pre-screening: Participants are pre-screened for medical history, including previous ALSFRS-R score and previous VC.

Screening Visit (Visit 1): After obtaining informed consent, screening procedures include medical history including ALS history and medications, concurrent medications, physical/neurological examination, hematology, chemistry, serology, coagulation markers, HIV, HBV and HCV serology, urinalysis, 12-lead electrocardiogram (ECG), vital signs (pulse, blood pressure, respiratory rate and temperature) height and weight. All women of child-bearing potential are tested by a serum pregnancy test.

*Base Line Visit (Visit 2): This visit is performed during the screening period and up to 10 days prior to the first dose administration. Eligible participants are subjected to neurological evaluations: ALSFRS-R, slow vital capacity (SVC), HHD, MMT and/or Hand grip strength, quality of life evaluation and depression and anxiety evaluation (as an indicator for potential effect on mood). FVC is also performed, as an indication for pre-treatment disease progression and is performed only during this visit. The participant's weight is captured as well. If decided on screening visit as necessary, a permanent port is placed.

**IPL344 IV administration starts within 6 weeks from screening

*** All participants receive daily treatment of IPL344 IV bolus injection or rapid infusion (using e.g. an electronic infusion pump) in a range of 1.7 mg/kg-5 mg/kg, unless the participant experiences a Grade ≥ 3 DLT (defined by CTCv4.03 published on Jun. 14, 2010), for a total of 28(+5) days. All participants are administered initially with 1.7 mg/kg IPL344 IV bolus or rapid infusion as a starting dose, with dose escalation by about 0.5 mg/kg IPL344 every 3-4 days (4 days is allowed only twice during dose escalation). Following each dose escalation, the drug is administered daily at the escalated dose until the next dose escalation. The dose is escalated until MTD or reaching a dose of 5 mg/kg IPL344 IV. In case of missing doses: If the delay is 1 day, the procedures at the original scheduled visit are performed. Participants with administrations delays of 3 days (i.e., 3 missed doses) discontinue treatment and return for the scheduled clinic visits. In the ease that an injection or infusion cannot be administered at a scheduled visit, it is administered as soon as possible.

First dose and dose escalation are performed in a clinic setting under the medical supervision on days 1, 4, 7 and 10 (+2 days). Prior to each of these dosing days, safety lab results, 12-lead electrocardiogram (ECG) and vital signs assessment are performed, reviewed and documented. These tests, performed before the first dose, are used as baseline values. In addition, blood sample for anti-drug antibodies are collected prior to the first dose as baseline for future testing. Note that the decision on dose escalation is per individual participant. In the case dose escalation continues beyond visit 6, all other dose escalations are also performed in a clinic setting. In evidence of DLT (AEs which are Grade ≥ 3 toxicity that is possibly, probably or certainly related to IPL344), then the dose level can be reduced by 0.5 mg/kg according to the criteria for dose escalation described in the following Table:

| CTC AE Toxicity Grade | Number of Partici-pants experi-encing AEs* | Action |
|---|---|---|
| Grade-1 | Zero-all | Escalate to next dose level |
| Grade-2 | Zero-all | Escalate to next dose level |
| Grade-3 | 1 | Based on a risk evaluation by the medical monitor, it is determined whether to continue the current dose or reduce dose to previous dose level and to rule the previous dose as MTD for this participant. If continued the current dose and Grade = 3 toxicities persist for > 24 hours, the dose is reduced. At reduced dose-if Grade 3 toxicities are observed for > 48, the Data safety monitoring board (DSMB) decides on continuation or stopping of treatment. |
| | 2 | Based on a risk evaluation by the medical monitor, it is determined whether to continue the current dose or reduce dose to previous dose level and to rule the previous dose as MTD for this participant. If continued with the current dose and Grade = 3 toxicities persist for > 24 hours, the dose is reduced. At reduced dose-if Grade 3 toxicities are observed for > 48, DMSB decides on continuation or discontinuation of treatment. Based on a risk evaluation by the DSMB, it is determined whether to allow the current dose to other participants in this study or to rule the previous dose as MTD for all participants. |
| Grade 4 or 5 | 1 | DLT; previous dose level is MTD for this participant. Treatment is stopped immediately and DSMB decides on continuation, treatment holiday or discontinuation of treatment for this participant. DSMB |

TABLE 3-continued

| Exemplary Detailed Schedule of Assessments for 28 days dose escalation treatment<br>Schedule of Events |
|---|
| also determines whether to allow the current dose for other participants or to rule the previous dose as MTD for all participants. |

[a] Medical history include, previous ALSFRS-R score; vital capacity (VC), prior ALS treatments and prior and concurrent medication use.

[b] Height and BMI only at screening visit.

[c] Vital signs measured are; blood pressure, heart rate, temperature, respiration rate, and pulse oximetry measurements. It is taken before any administration, 15-20 minutes, and 1-hour post administration during home visit, and 15-20 minutes, 1 and 4 hours post administration during clinic visit.

[d,e,f,g] Safety labs-collected and reviewed prior to each dose escalation.

[h] 12-lead electrocardiogram (ECG) is taken before any clinic visit administration and 15-20 minutes, 1 and 4 hours post administration.

[i] Self-administration training: any time after the last dose escalation until day 27. The qualified health professional (physician or nurse) provides training for a) drug preparation b) self-administration; and c) routine care of the central venous catheter.

[j] AEs are assessed from the first dose of administration and at each study visit before any study procedures are performed as well as after study procedures are performed. Any new medical event that accrues after signing the ICF is captured as medical history.

[k] Prior and concurrent medication use including dietary supplements.

[l]PK-the assessment of IPL344 PK is performed at Day 1 following first dose, each dose-escalation administration and on Day 28. A 3-4 mL sample of blood is collected in a plasma tube prior to the start of IPL344 administration and at 5, 10, 20, 30, 40, 60 and 120 minutes following administration,

[m] Cannula/CVC/PICC line or Port removal-only participants that discontinue treatment. The dose escalation study is conducted in accordance with the following guidelines: GCP: Consolidated Guideline (International Conference on Harmonisation of Technical Requirements for the Registration of Pharmaceuticals for Human Use, May 1996). Declaration of Helsinki: Brazil, 2013 Local country guidelines for conducting clinical trials Study Inclusion Criteria:

1. Male or female participants ages ≥ 18 to 80 years.
2. Consenting participants fulfilling the El Escorial criteria for probable and definite ALS (sporadic and familial).
3. Participant has ALSFRS-R score of > 20 and a disease progression rate greater than 0.55 ALSFRS-R points per month in average over at least 4 months prior to latest ALSFRS-R test or a decline of at least 3 points in ALSFRS-R score within the last 4 months prior to the latest ALSFRS-R. test. The latest ALSFRS-R test is no more than 6 weeks before screening visit.
4. Previous data of Force Vital Capacity (FVC) of ≥ 60 at least 3 months before screening and not more than 12 months.
5. Written informed consent consistent with International Conference on Harmonization (ICH)-Good Clinical Practice (GCP) and local laws, signed prior to any study procedures being performed. (including any required washout).
6. BMI 18.5 to 30 kg/m$^2$ inclusive and weigh at least 50 kg and no more than 100 kg.
7. If taking Riluzole or edaravone, participant must be on a stable dose for ≥ 30 days prior to Day 1 and expected to remain at that dose until the final study visit.
8. Medically able to undergo the study procedures, and to adhere to the visit schedule at the time of study entry.
9. Female participants are non-pregnant, non-lactating at screening, as documented by a negative human chorionic gonadotropin (hCG) beta-human chorionic gonadotropin (β-hCG).
10. Women of child-bearing potential and males whose partners are women of child-bearing potential should practice contraception throughout the trial e.g. condom use by male, contraception by female.

Study Exclusion Criteria: Participants who meet any of the following criteria are not eligible to enter this study:

1. Concurrent therapy that, in the PI's opinion, interferes with the evaluation of the safety or efficacy of the study medication.
2. Co-existing psychiatric disorder which started before ALS diagnosis, excluding a depression disorder.
3. Presence of any other condition or circumstance that, in the judgment of the Investigator, might contra indicate or increase the risk to the participant or decrease the chance of obtaining satisfactory data to achieve the objectives of the study.
4. Use of tracheostomy, tracheostomy invasive mechanical ventilation [TIMV].
5. History of HIV, positive HBV or HCV serology.
6. Participants suffering from significant cardiac, or any other disease that may endanger the participant or interfere with the ability to interpret the results.
7. Participants with active infections.
8. Documented Active cancer.
9. Lactating or pregnant women at Screening or Baseline (as documented by a negative beta-human chorionic gonadotropin [β-hCG] (or human chorionic gonadotropin [hCG]).
10. Treatment with another investigational drug, biological agent, or device within 2 months of first dose, or investigational cell therapy within 6 months of first dose.
11. Participants that reside 75-minutes drive or more from the site.
12. Women of child-bearing potential or males whose partners are women of child-bearing potential, unwilling or unable to use an effective method of contraception throughout the trial.

Example 2

IPL344 Treatment Protocol

Table 4 below summarizes a protocol for intravenous (IV) administration of IPL344 for the treatment of ALS of some embodiments of the invention.

TABLE 4

| IPL344 for the treatment of ALS | |
|---|---|
| Treated population | Subjects with ALS according to the above criteria |
| Dose and route of Administration | IPL344 is administered intravenously (IV) on a daily basis (every 24 ± 6 hours) via a cannula or permanent port, PICC line OR central venous catheter or central venous catheter (CVC, e.g. Hickman line). For subjects (e.g. subjects with known non-accessible veins), a placement of permanent PICC line, CVC or port is offered for administration of IPL344 and scheduled prior to treatment period. IV administration by a cannula in these subjects is optional in cases of CVC, PICC or port mal-function such as an infection, blood clot etc. For other subjects, if later during the dosing period the injection is difficult using the cannula, a port, CVC or PICC line is placed at any required time.<br>Dose range of IPL344 is 2-5 mg/kg,<br>(IPL344-dose is determined for base peptide without acetate and impurities as detailed in Example 1, materials and methods, hereinabove) |
| Treatment Duration | Typically, each subject receives daily IV IPL344 for 28 days; following subjects can continue treatment at the physician discretion and subject's agreement. |
| Mode of Administration | Drug administration can be performed in the clinic or at home by a qualified health professional e,g, a physician or a trained nurse. After adequate training also by self-administration or by trained care giver.<br>The subject receives daily treatment of IPL344 IV bolus injection or rapid infusion using an electronic pump in a range of 2 mg/kg-5 mg/kg, unless the subject experiences a Grade ≥3 DLT (defined by CTCv4.03 published on Jun. 14, 2010).<br>In case of dose escalation, typically, the administered dose is escalated by 0.5 mg/kg in every step and can be escalated until MTD or reaching a dose of 5 mg/kg IPL344 IV.<br>In the event of evidence of hypersensitivity including the following symptoms: sinus tachycardia, heavy breathing or rash (along the veins or elsewhere), if confirmed by the medical monitor that the effects are attributed to hypersensitivity, IPL344 is administered in the next day in a clinic setting, by IV infusion (slow dripping), |

TABLE 4-continued

| IPL344 for the treatment of ALS | |
|---|---|
| | Drug hypersensitivity is not considered a dose limiting toxicity as long as it is treatable by desensitization procedure.<br>If following the desensitization process with IV infusion the dose is well tolerated-treatment can continue as planned. In this case an escalation of dose is also permitted according to the planned schedule.<br>If the desensitization process fails, the IPL344 treatment for this subject is discontinued. |
| Efficacy Assessment | Effect of IPL344 treatment on the progression of the disease is assessed by:<br>ALSFRS-R<br>Respiratory function: SVC (slow vital capacity)<br>Muscle strength: MMT (Manual muscle testing), HHD (Hand held dynamometry) and/or Hand grip strength.<br>Cognitive/behavior function: Depression evaluation [by the ALS Depression Inventory 12 (ADI-12), the Beck Depression Inventory (BDI) questionnaire and/or the anxiety Hospital Anxiety Depression Scale (HADS) questionnaire.<br>ALSERS-R, respiratory and muscle functional tests are performed by a physician or physiotherapist trained by NEALS, using spirometer and dynamometer according to NEALS guidelines for clinical trials. |

Example 3

Interim Results of an Open-Label Phase 1/2A IPL344 Treatment Clinical Trial

Eight patients have completed a 28 days safety study with IPL344. Patients started treatment at ALSFRS-R values between 22 and 38 (on a 48-point scale). Treatment began at 1.7 mg/kg and increased by 0.5 mg/kg every three to four days to the maximum dose of 3.2 mg/kg. Following, treatment maintained at a daily dose of 3.2 mg/kg. Eight additional patients are being recruited to a second cohort with a daily dose of 4.5 mg/kg.

Overall, IPL344 established a favorable safety and tolerability profile. No drug-related adverse events have been reported.

Figure 2:
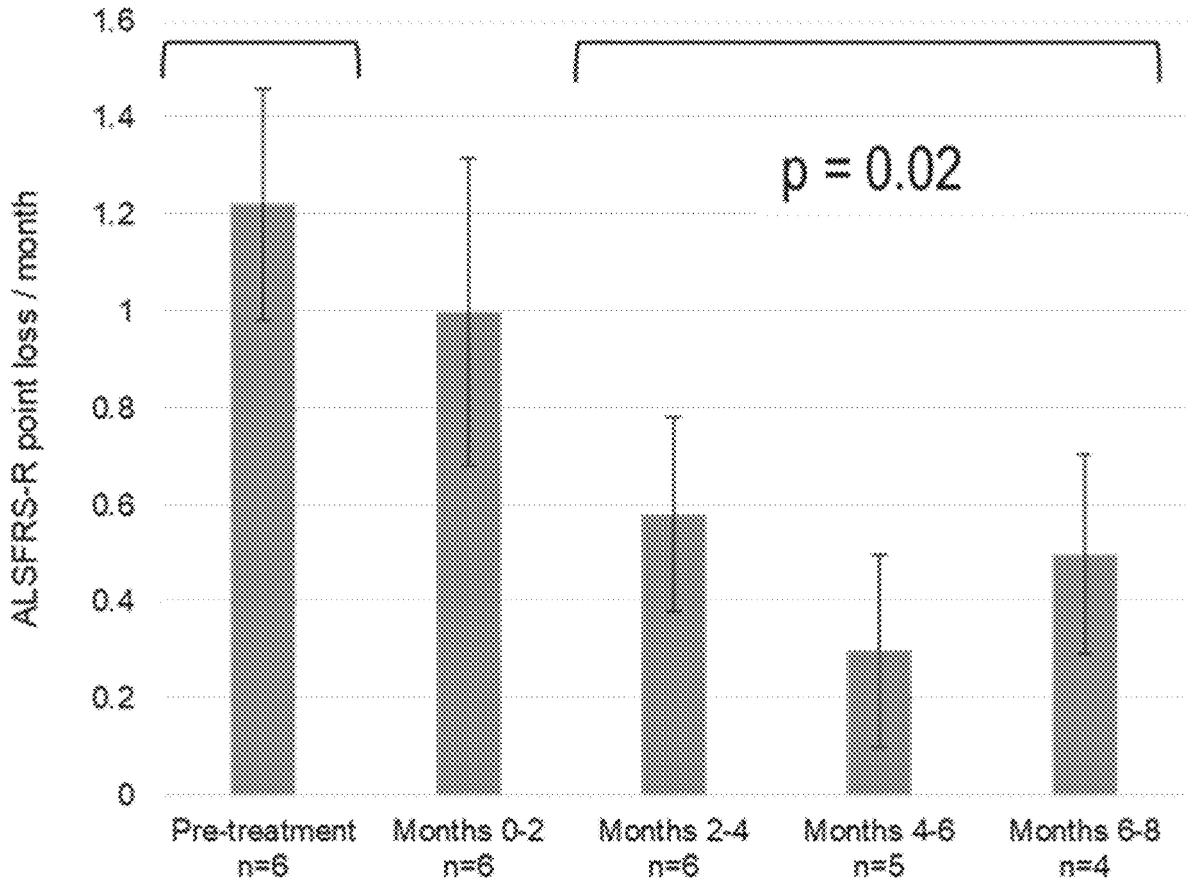
FIG. 2 is a graph demonstrating ALS disease periodic progression rates, evaluated by ALSFRS-R point loss per month, in ALS patients treated with 3.2 mg/kg IPL344.

Changes in functional impairment and respiratory functions were observed in the first six patients who received treatment for more than four months (range 4-13 months, average 8 months). During that period, patients experienced a 49% slower decline (p=0.08) in existing abilities compared to their decline prior to treatment, as measured by ALS Functional Rating Scale-Revised (ALSFRS-R) scores that cover speech, swallowing, dressing and hygiene, among other daily functions (FIG. 1). In advanced stages of disease, ALSFRS-R scores decline in a linear manner, meaning that physicians can predict a patient's progression over a given period of time. The projected linear deterioration rate is an established surrogate for a placebo group in early clinical trials in ALS; it is based on a large body of published research, studying disease progression in thousands of untreated ALS patients. During the average eight months of treatment, patients lost an average of 4.7 fewer ALSFRS-R points than that projected based on their pre-treatment progression. Notably, the benefits started mainly after the first two months of treatment (FIG. 2). Beyond that two-months mark, IPL344 slowed disease progression even further, by 61% (p=0.03). Lung function was measured using the slow vital capacity (SVC), which measures the maximum volume of gas expired during a slow expiration. The six patients lost 1.3% SVC per month, on average, compared to an average of 3.1% in the general ALS population. This amounted to a 57% decline, or improvement, in the rate of lung function deterioration.

Both measures of functional impairment and lung function are well-established predictors of survival and the results indicate positive impacts on patients' quality of life.

In addition, IPL344 is known to activate the Akt signaling pathway directly within the cells. The Akt pathway is responsible for protecting cells against destructive processes that are the main drivers of ALS: cell-death, inflammation and aggregation of misfolded proteins. Akt is down-regulated in ALS, exposing cells to these destructive processes. However, activating Akt in patients remains a challenge as many potential Akt activation-pathways are disrupted during the disease. Biomarker data from patients in this Phase 1/2a study demonstrated, in a statistically significant manner, that the treatment protocol restored. Akt activation levels in patients back to their normal levels; confirming target engagement under disease conditions, and IPL344's ability to activate the pro-survival Akt pathway in patients suffering from ALS.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. It is the intent of the applicant(s) that all publications, patents and patent applications referred to in this specification are to be incorporated in their entirety by reference into the specification, as if each individual publication, patent or patent application was specifically and individually noted when referenced that it is to be incorporated herein by reference. In addition, citation or identification of any reference in this application shall not be construed as an admission that such reference is available as prior art to the present invention. To the extent that section headings are used, they should not be construed as necessarily limiting. In addition, any priority document(s) of this application is/are hereby incorporated herein by reference in its/their entirety.

What is claimed is:

1. A method of treating amyotrophic lateral sclerosis (ALS) in a human subject in need thereof, the method comprising intravenously (IV) administering, on a daily basis, to the subject 2-5 mg/kg of a peptide consisting of an amino acid sequence as set forth in SEQ ID NO: 1, wherein the peptide is formulated in Dulbecco's phosphate buffered saline (DPBS) at a concentration of 50 mg/ml, said DPBS comprising calcium and magnesium, wherein said administering is by bolus injection or IV infusion, thereby treating the ALS in the subject.

2. The method of claim 1, further comprising monitoring said subject by ALS Functional Rating Scale (ALSFRS); respiratory function; muscle strength and/or cognitive function following the treating.

3. The method of claim 1, wherein said ALS is rapid progression ALS.

4. The method of claim 1, wherein said ALS is non-slow progression ALS.

5. The method of claim 1, wherein the method comprises administering 2.5-4.5 mg/kg of the peptide.

6. The method of claim 1, wherein the method comprises administering 3-4 mg/kg of the peptide.

* * * * *

SEQUENCE LISTING

```
<160> NUMBER OF SEQ ID NOS: 1

<210> SEQ ID NO 1
<211> LENGTH: 7
<212> TYPE: PRT
<213> ORGANISM: Artificial Sequence
<220> FEATURE:
<223> OTHER INFORMATION: Synthetic peptide
```

-continued

```
<400> SEQUENCE: 1

Leu Pro Pro Leu Pro Tyr Pro
1               5
```